United States Patent [19]

Nakabayashi

[11] Patent Number: 5,028,872
[45] Date of Patent: Jul. 2, 1991

[54] MAGNETIC RESONANCE IMAGING SYSTEM

[75] Inventor: Kazuto Nakabayashi, Ootawara, Japan

[73] Assignee: Kabushiki Kaisha Toshiba, Kawasaki, Japan

[21] Appl. No.: 393,008

[22] Filed: Aug. 11, 1989

Related U.S. Application Data

[63] Continuation of Ser. No. 164,926, Mar. 4, 1988, abandoned.

[30] Foreign Application Priority Data

Mar. 6, 1987 [JP] Japan .................. 62-52421

[51] Int. Cl.⁵ .................. G01R 33/20
[52] U.S. Cl. .................. 324/318
[58] Field of Search .......... 324/318, 320, 322; 335/299, 301; 128/653

[56] References Cited

U.S. PATENT DOCUMENTS

| | | | |
|---|---|---|---|
| 4,564,812 | 1/1986 | Van Dijk | 324/309 |
| 4,613,820 | 9/1986 | Edelstein et al. | 324/318 |
| 4,642,569 | 2/1987 | Hayes et al. | 324/318 |
| 4,725,781 | 2/1988 | Röschmann | 324/318 |
| 4,785,246 | 11/1988 | Sugimoto | 324/318 |

FOREIGN PATENT DOCUMENTS

| | | |
|---|---|---|
| 0151726 | 8/1985 | European Pat. Off. . |
| 3511750 A1 | 10/1986 | Fed. Rep. of Germany . |
| 3621107 A1 | 1/1987 | Fed. Rep. of Germany . |
| 59-77348 | 5/1984 | Japan . |

Primary Examiner—Hezron E. Williams
Assistant Examiner—Louis M. Arana
Attorney, Agent, or Firm—Foley & Lardner

[57] ABSTRACT

A magnetic resonance imaging (MRI) system which includes a main shield member arranged in the cylindrical housing; and a sub shield member which is electrically connected to the main shield member and is arranged outside the housing to cover a region where the object under examination is placed. Thus, a magnetic resonance signal can be prevented from being electromagnetically mixed with the disturbance electromagnetic wave, and an MRI image can be accurately formed. The sub shield member covers only a desired region of a patient. For this reason, the patient can satisfactorily receive external light, the feeling of oppression can be greatly eliminated, and the shield member can be rendered compact. The sub shield member includes a lid shield member which is detachably attached to the main shield member, and a cover shield member which covers a portion extending from the main shield member. According to the intensity of a disturbance electromagnetic wave, the lid shield member and the cover shield member are selectively employed.

15 Claims, 6 Drawing Sheets

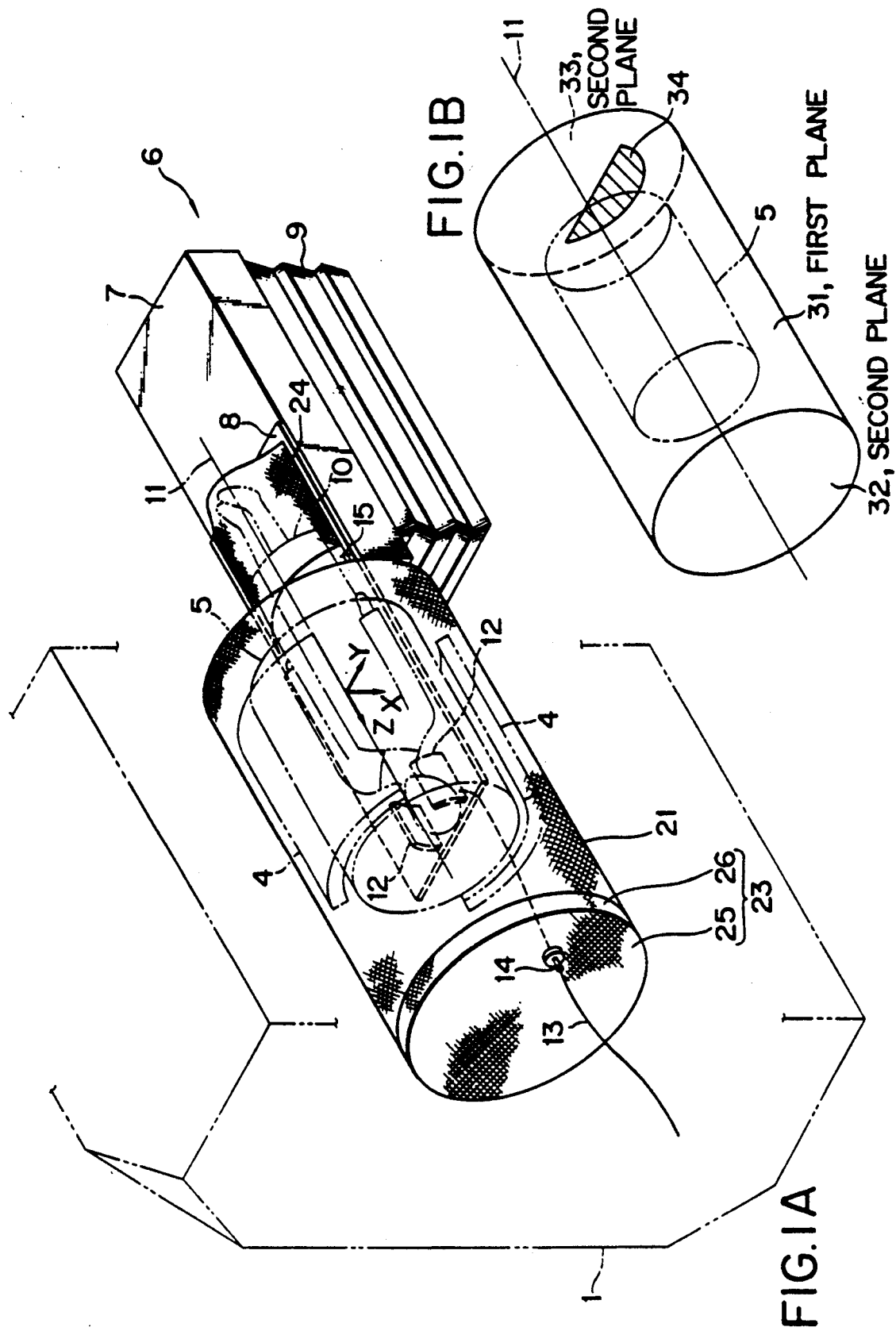

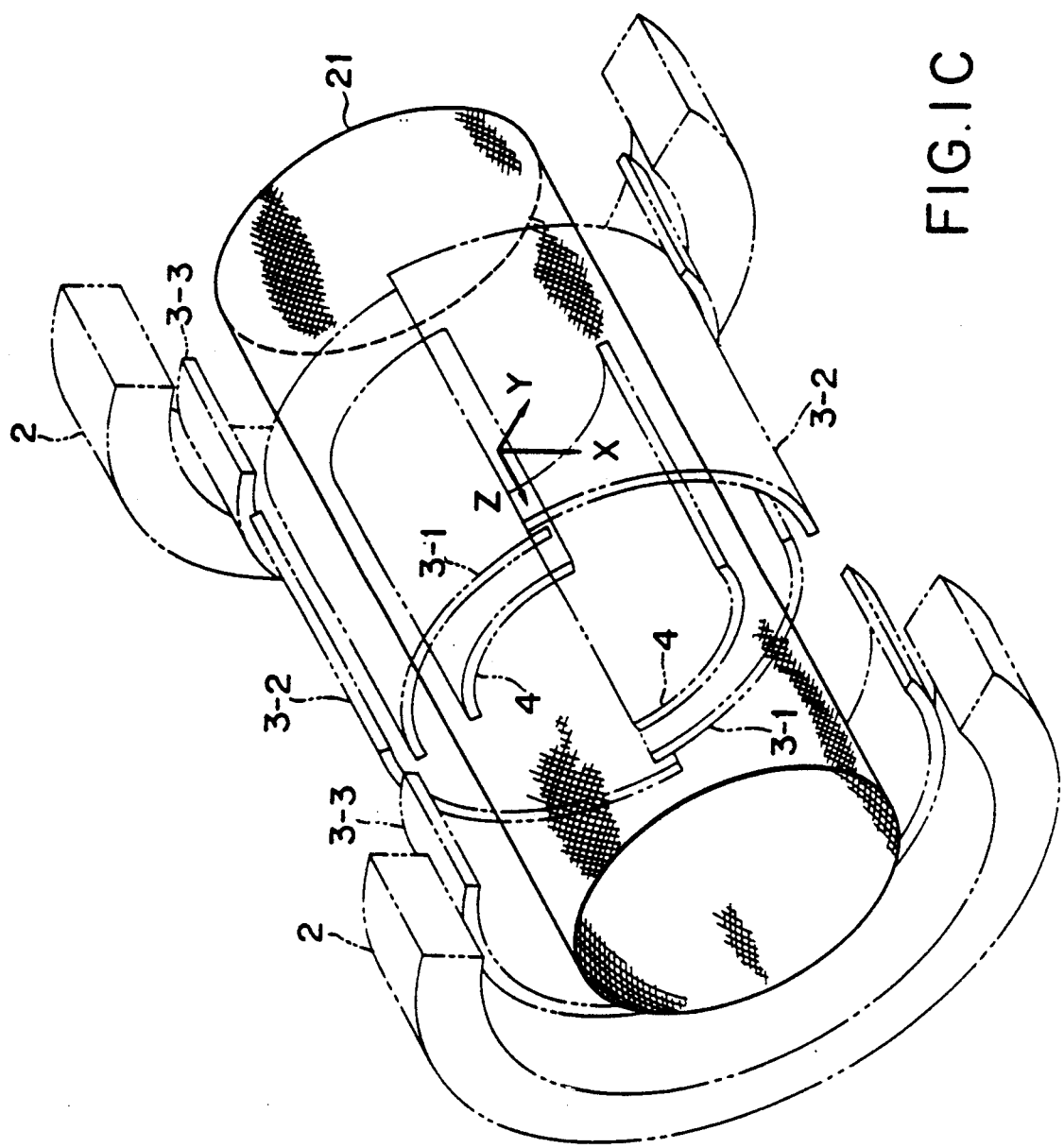
FIG.IC

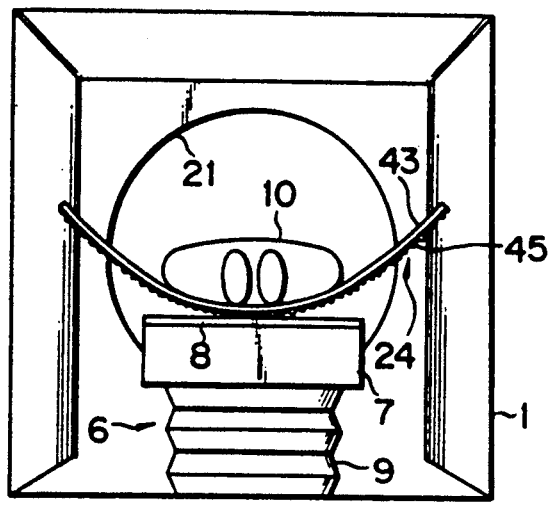 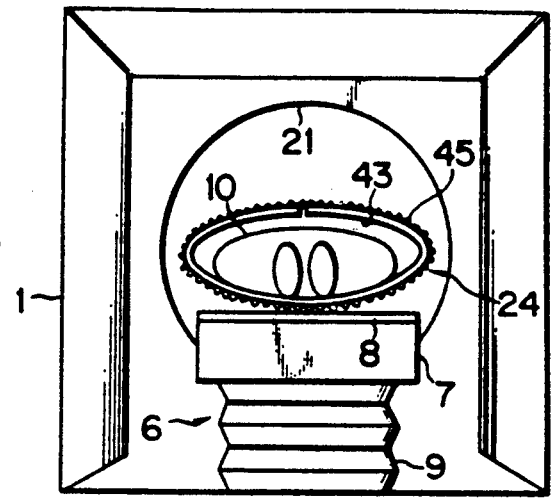
FIG. 4A    FIG. 4B
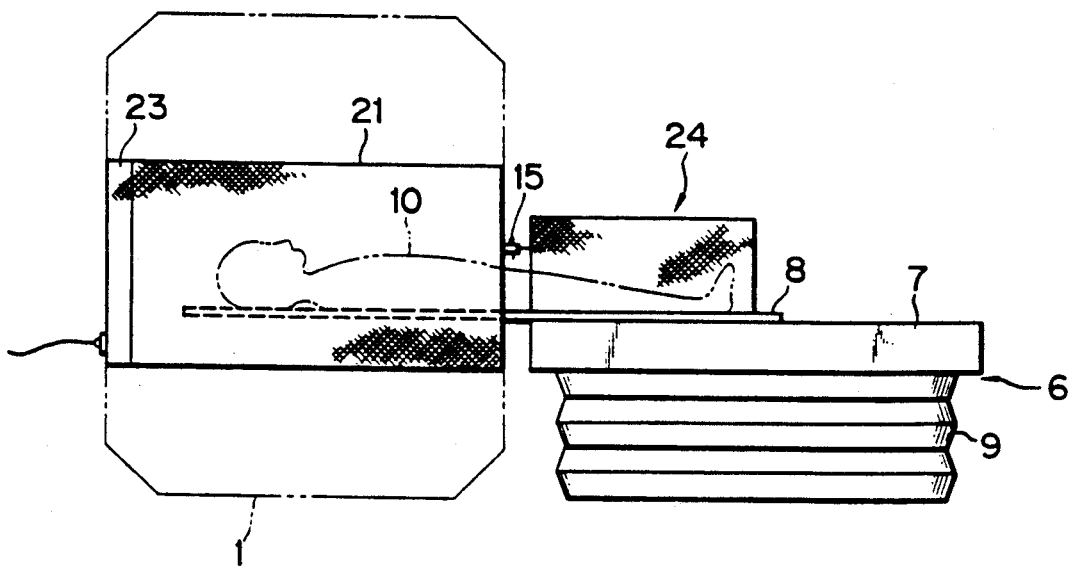
FIG. 4C

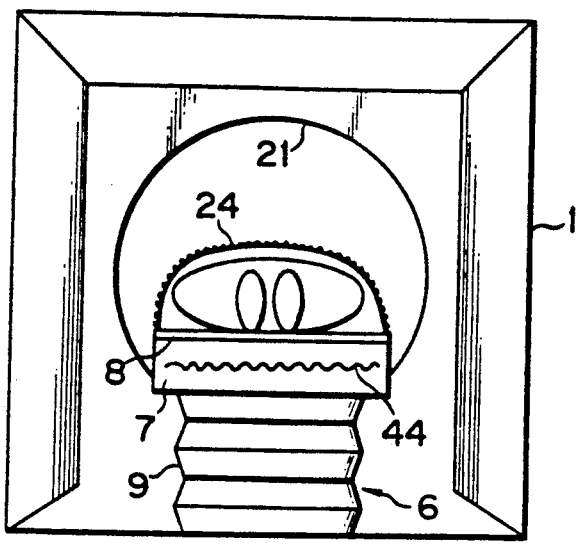
F I G. 5A
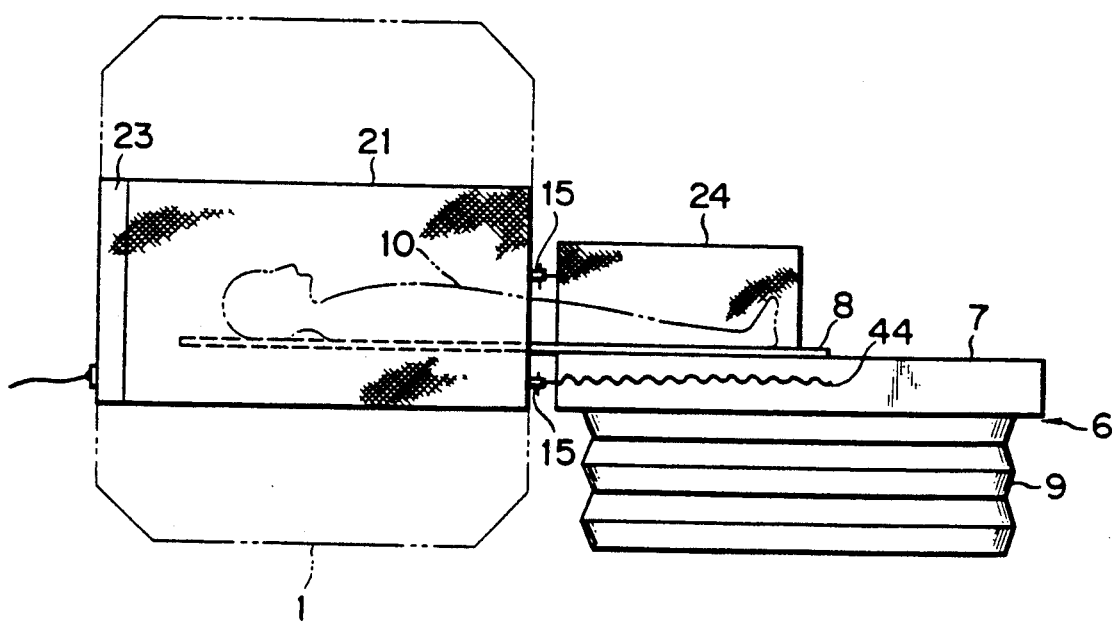
F I G. 5B

MAGNETIC RESONANCE IMAGING SYSTEM

This application if a continuation of application Ser. No. 07/164,926, filed Mar. 4, 1988 now abandoned.

BACKGROUND OF THE INVENTION

1. Field of the Invention

The present invention relates to a magnetic resonance imaging (MRI) system having a self shield for shielding a disturbance electromagnetic wave radiated inside an examination space of a static homogeneous magnetic field being generated where an object (patient) under examination is placed.

2. Description of the Related Art

In a magnetic resonance imaging system, magnetic resonance signals generated by the object patient excited with a magnetic field and a radio frequency pulse are collected from an entire plane simultaneously, and an MRI image is reconstructed based on the signals. The magnetic resonance signal is very weak. For this reason, it is necessary to prevent the magnetic resonance signal from being mixed with a disturbance electromagnetic wave.

For this purpose, the magnetic resonance imaging system is installed in a shield room for shielding the disturbance electromagnetic wave. Thus, the magnetic resonance signal can be shielded from the disturbance electromagnetic wave.

However, the imaging system includes a patient couch on which a patient is positioned. Therefore, a shield room is required to be a relatively large space. In order to obtain a satisfactory shield effect, the construction cost of the shield room is extremely high.

Japanese Pat. Disclosure (Kokai) No. 59-77348 discloses the following RF self shield. The self shield comprises a conductive member arranged in a housing of the imaging system, and a conductive housing for covering a portion of a patient extending outside the conductive member in a tunnel-like shape.

However, the examination space in the housing is cylindrical, and the interior of the conductive housing has an elongated space. For this reason, a patient in the examination space to some extent cannot receive external light, and external air cannot be supplied therein. Thus, the patient suffers from a feeling of oppression from the conductive housing. In particular, when a patient is very sick, the feeling of oppression adversely affects him in respect to the patient's mental health. In addition, the conductive housing must have an opening with a lid, through which a patient can enter the conductive housing. This results in a need for a very large conductive housing.

Furthermore, the conventional self shield has the following drawbacks.

The X gradient coils, Y gradient coils and Z gradient coils (3-1, 3-2, 3-3 in FIG. 1C) are actually concentrically superimposed within static field magnetic coil 2 and are preferably constructed so as to receive at least a portion of the object therein. The RF transmit/receive coil 4 (FIGS. 1A, and 1C) is also of conventional design and is designed so as to cause the RF magnetic field to be perpendicular to the static magnetic field. The conductive member is arranged near the gradient coil. An eddy current is sometimes induced in the conductive member due to the magnetic gradient pulses from the coil. A magnetic field is generated by the eddy current in the conductive member. The magnetic field is harmful to the receiving characteristics of a receiving coil for receiving the magnetic resonance signal. As a result, an the MRI image may be degraded.

Moreover, the frequency of a current flowing through the conductive member may be tuned to that of the magnetic resonance signal. As a result, magnetic coupling occurs between the receiving coil and the conductive member. An electric wave is thus coupled from the conductive member to the receiving coil. For this reason, the magnetic resonance signal cannot be accurately received, and the MRI image is degraded.

SUMMARY OF THE INVENTION

It is an object of the present invention to provide a magnetic resonance imaging system having a compact self shield for shielding a disturbance electromagnetic wave to allow an MRI image to be accurately formed, and for minimizing the feeling of oppression to a patient.

It is another object of the present invention to provide a magnetic resonance imaging system which can prevent an eddy current and magnetic coupling generated in a self shield.

According to the present invention, there is provided a magnetic resonance imaging system, wherein the system comprises a housing which may be cylindrical. The housing includes an examination space in which at least a portion of an object is placed; a magnet, arranged to surround the examination space, for generating a static magnetic field within the examination space; a gradient-coil subsystem, arranged also to surround the examination space, for imposing a gradient magnetic fields on the static magnetic field; a radio frequency coil for generating a high frequency magnetic field signal, exciting the object and receiving a magnetic resonance signal generated by the portion of the object;

a main shield member arranged in the housing; and a sub shield member which is electrically connected to the main shield member and is arranged partially outside the housing to shield a region where the portion of the object extending from the housing is positioned.

The sub shield member covers only a desired portion of a patient. For this reason, the patient can satisfactorily receive external light, and the feeling of oppression can be greatly eliminated. Since the sub shield member covers only the desired region of the patient, it need not be formed into a tunnel-like shape unlike in a conventional system, and can be rendered compact.

The sub shield member comprises a lid shield member which is detachably attached to the main shield member, and a cover shield member which covers a portion extending from the main shield member. Therefore, when the intensity of a disturbance electromagnetic wave is relatively low, the disturbance electromagnetic wave can be shielded by only the main shield member. When the intensity of the electromagnetic wave is relatively high, the lid shield member of the sub shield member can also be attached to the main shield member. When the intensity of the disturbance electromagnetic wave is much higher, the cover shield member of the sub shield member need only cover at least a portion of a patient extending from the main shield member. Thus, a magnetic resonance signal can be prevented from being electromagnetically mixed with the disturbance electromagnetic wave, and an MRI image can be accurately formed.

The main shield member comprises a plurality of shield segments formed of a conductive material, and insulating members interposed between adjacent shield segments. Thus, an eddy current can be prevented from being generated in the main shield member. The main shield member comprises a plurality of shield segments formed of a conductive material, and capacitors interposed between adjacent shield segments. Thus, generation of magnetic coupling between the main shield member and a radio frequency coil can be prevented.

BRIEF DESCRIPTION OF THE DRAWINGS

FIG. 1A is a perspective view of a magnetic resonance imaging system according to the present invention;

FIG. 1B is a view illustrating a shield member shown in FIG. 1A;

FIG. 1C is a perspective view illustrating an arrangement of the magnetic resonance imaging system shown in FIG. 1A;

FIGS. 4A, 4B, and 4C show a third modification of the present invention, in which FIGS. 4A and 4B are front views of a magnetic resonance imaging system, and FIG. 4C is a side view of the imaging system; and FIGS. 5A and 5B show a fourth modification of the present invention, in which FIG. 5A is a front view of a magnetic resonance imaging system and FIG. 5B is a side view of the imaging system.

DETAILED DESCRIPTION OF THE PREFERRED EMBODIMENTS

Figure 2A:
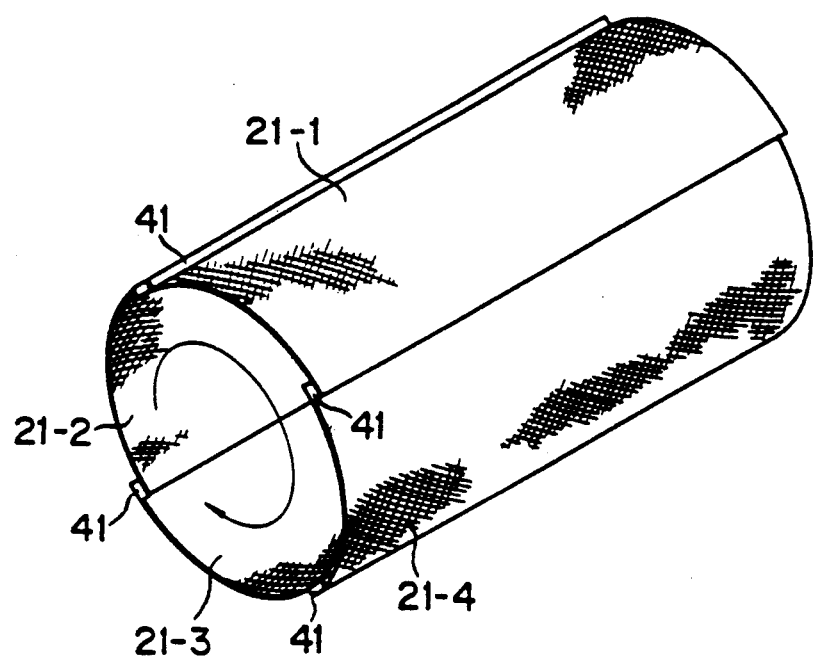
FIG. 2A is perspective view of a shield member according to a first modification of the present invention.

FIGS. 1A and 1C show a magnetic resonance (MR) imaging system according the present invention, for imaging information based on a density distribution of specific nuclear spins and/or a relaxation time of resonance at a specific portion of an object (patient) 10 to be examined.

The system comprises non-conductive, non-magnetic cylindrical housing having resistive-type magnets 2. Magnets 2 generate static magnetic field as a main magnetic field in a Z direction as is shown in FIGS. 1A and 1C, usually in a direction coincident with axis 11 of object 10. As is shown in FIG. 1C, a pair of X-axis gradient coils 3-1, a pair of Y-axis gradient coils 3-2, and a pair of Z-axis gradient coils 3-3 are arranged coaxially with magnets 2. X-axis gradient coils 3-1 face each other, and so do Y-axis gradient coils 3-2. The X axis of gradient coils 3-1 and the Y axis of gradient coils 3-2 intersect at right angles with each other. Z-axis gradient coils 3-3 are located at the ends of a unit comprised of X-axis gradient coils 3-1 and Y-axis gradient coils 3-2. Z-axis gradient coils 3-3 generate gradient magnetic fields which create position-dependent magnetic fields to determine the position of that slice of object 10 which is to be imaged. X-axis gradient coils 3-1 and Y-axis gradient coils 3-2 generate gradient magnetic fields for reading and encoding an MR signal generated from object 10.

Radio frequency (RF) coils 4 are arranged radially inside X-axis gradient coils 3-1 and Y-axis gradient coils 3-2. Examination space 5, in which a portion to be examined of object 10 is placed, exists radially inside RF coils 4. RF coils 4 are used to transmit an excitation pulse (in the form of an RF electromagnetic field) to the portion of object 10 to excite nuclear spin by the MR, and to receive the MR signal generated from the nuclear spin by the MR. RF coils 4 are positioned such that an RF electromagnetic field is perpendicular to the static magnetic field.

The imaging system comprises patient couch 6. Patient couch 6 comprises base 7, slide plate 8 which is arranged on the upper surface of base 7 and is slidable in a horizontal direction, and lift 9 for vertically moving base 7. Patient 10 lies on the upper surface of slide plate 8. After slide plate 8 is lifted upward by lift 8 to a predetermined height, slide plate 8 slides toward the interior of frame or housing 1. A portion to be examined of patient 10 is thus placed in examination space 5.

Magnets 2 apply a uniform static magnetic field to object 10. Predetermined gradient magnetic fields are superposed on the static magnetic field, and are applied to a predetermined portion of object 10, including a specific slice to be imaged. RF electromagnetic field for exciting nuclear spin is applied in a direction perpendicular to the static magnetic field. As a result, MR signals are generated in the predetermined portion only. After the application of the excitation pulse has been stopped, the MR signal generated from the nuclear spin is received and Fourier-transformed, so that a spectrum of an angular frequency of a specific nuclear spin is determined. A tomographic image, i.e., an MR image, can be reconstructed by a computed tomography technique.

Receiving coil 12 may be arranged in examination space 5 and receives a magnetic resonance signal exited from the patient.

The system of the present invention comprises a shield member (RF self shield) for shielding a disturbance electromagnetic wave radiated inside examination space 5. The shield member is constituted by main shield member 21 arranged inside housing 1, and a sub shield member comprising member 23 and member 24, arranged outside housing 1. The sub shield member is constituted by lid shield member 23 which is arranged at a side from which patient 10 does not enter and is fitted in main shield member 21, and cover shield member 24 which is arranged at a side from which patient 10 enters and covers legs (at least a portion of a patient extending from the main shield member) of patient 10.

Main shield member 21 is a cylindrical member arranged to have axis 11 as the center. Member 21 is arranged radially outside RF coils 4 and radially inside gradient coils 3-1, 3-2, 3-3. Member 21 is open to an extending direction of axis 11. Member 21 is formed of a conductive material, e.g., a metal foil, a metal net, or the like. Therefore, as will be described later, a disturbance electromagnetic wave incident in examination space 5 is shielded by main shield member 21. Member 21 also shields noise components generated by coils 2 and 3-1, 3-2, 3-3. Main shield member 21 need not be formed into an annular shape. For example, member 21 may have a polygonal section, e.g., a rectangular or triangular section. Member 21 need not be a cylindrical member formed of a single member, and may be formed by combining a plurality of members.

The lid shield member 23 of the sub shield member closes the opening of the main shield member 21, and comprises disk-like portion 25, and a flange 26 extending from portion 25. Flange 26 is fitted in main shield member 21. With flange 26, lid shield member 23 is attached/detached to/from main shield member 21. Lid shield member 23 is electrically connected to main shield member 21. Member 23 is formed of a light-transmission conductive material such as a metal net or an expand metal. Thus, patient 10 lying inside examination space 5 can receive external light and external air. For this reason, the feeling of oppression of the patient can be eliminated. When receiving coil 12 is arranged inside examination space 5, an EMI filter and connector 14 for cable 13 extending from receiving coil 12 are provided to lid shield member 23.

Cover shield member 24 of the sub shield member covers a portion of a patient extending outside frame 1. Cover shield member 24 is formed of a light-transmission conductive material and into a cylindrical or semi-cylindrical shape. Thus, the feeling of oppression of the patient can be eliminated. Cover shield member 24 may be formed of a conductive fabric. In this case, the fabric shield member can cover a patient as a normal blanket. Thus, the patient does not suffer from the feeling of oppression. Member 24 is electrically connected to main shield member 21 through connector 15. A large number of portions of member 24 may be electrically connected to main shield member 21.

The principle of the shield member will be described with reference to FIG. 1B.

As shown in FIG. 1A, the shield member is assumed to be constituted by a predetermined space as follows. More specifically, a cylindrical imaginary area surrounding axis 11 and examination space 5 is assumed to be first area 31. Flat imaginary planes facing axis 11 and outside examination space 5 are assumed to be second areas 32 and 33. Second area 32 is arranged at a side from which a patient does not enter, and second area 33 is arranged at a side from which the patient enters.

Theoretically, it is most preferable that the shield member is provided to cover the entire examination space. However, if the intensity of a disturbance electromagnetic wave is low, when only an electromagnetic wave radiated inside the examination space through first area 31 is shielded, a nuclear magnetic resonance signal is not almost influenced by the disturbance electromagnetic wave. For this reason, when the intensity of the disturbance electromagnetic wave is low, main shield member 21 corresponding to the first area shields an electromagnetic wave propagating through the first area.

When the intensity of a disturbance electromagnetic wave is high, an electromagnetic wave may be radiated inside examination space 5 through second areas 32 and 33. For this reason, at the side from which the patient does not enter, lid shield member 23 corresponding to second area 32 shields an electromagnetic wave propagating through second area 32.

At the side from which the patient enters, theoretically entire second area 33 is preferably shielded. However, the patient extends through second area 33. For this reason, it is very difficult to shield the entire second area 33. Furthermore, the patient is a conductor, and the legs of the patient (at least a portion of a patient extending from the main shield member) receive a disturbance electromagnetic wave. The disturbance electromagnetic wave is transmitted to a portion to be examined through the body of the patient. In this invention, the legs of the patient are covered by cover shield member 24. For this reason, the legs do not receive the disturbance electromagnetic wave. In other words, the disturbance electromagnetic wave cannot be radiated inside examination space 5 through portion 34 (a hatched plane region in FIG. 1B) of second area 33. That is, at least part of an electromagnetic wave radiated through second area 33 can be shielded by cover shield member 24.

Therefore, when the intensity of the disturbance electromagnetic wave is relatively low, the disturbance electromagnetic wave can be shielded by only the main shield member 21. When the intensity of the disturbance electromagnetic, wave is relatively high, lid shield member 23 of the sub shield member can be fitted in main shield member 21. When the intensity of the disturbance electromagnetic wave is much higher, cover shield member 24 of the sub shield member can cover the legs (at least a portion of a patient extending from the main shield member) of the patient. Thus, the magnetic resonance signal can be prevented from being electromagnetically mixed with the disturbance electromagnetic wave, and an MRI image can be accurately formed. In this invention, since the sub shield member is constituted by three relatively small members, the shield member (self shield) can be very compact in size.

According to the present invention, the shield member is formed of a light-transmission conductive material such as a metal net or expand metal. A patient placed inside the examination space can receive external light and air. For this reason, the patient can be free from the feeling of oppression. Unlike in the conventional system, the patient is not covered by a tunnellike large member. The shield member of the present invention can remarkably eliminate the feeling of oppression of the patient as compared to the conventional shield member.

FIG. 2A shows a first modification of the present invention.

In FIG. 2A, main shield member 21 is divided into four shield segments 21-1, 21-2, 21-3, and 21-4. Insulating members 41 are interposed between adjacent shield segments 21-1 to 21-4. Thus, shield segments 21-1 to 21-4 are electrically insulated from each other. Each insulating member 41 is, e.g., an insulating sheet. The number of shield segments used is not intended to be limited to four.

In this modification, generation of an eddy current in main shield member 21 can be prevented. More specifically, as shown in FIG. 1C, main shield member 21 is arranged near gradient magnetic field coils 3-1 to 3-3. For this reason, when member 21 is formed by a single conductive member into a cylindrical shape, an eddy current may be induced in the main shield member as indicated by an arrow in FIG. 2A. A magnetic field is generated in the space of the main shield member by the eddy current, and impairs the receiving characteristics of RF coil 4. Thus, an MRI image may be degraded.

In this modification, as described above, main shield member 21 is divided into shield segments 21-1 to 21-4, and shield segments 21-1 to 21-4 are electrically insulated from each other. For this reason, even if an eddy current is generated in shield segments 21-1 to 21-4 by coils 3, the eddy current is divided by segments 21-1 to 21-4, and does not generate a magnetic field in the main shield member. For this reason, the RF coil is not affected by the magnetic field of the eddy current. As a result, the receiving characteristics of the RF coil and the MRI image can be prevented from being degraded.

Figure 2B:
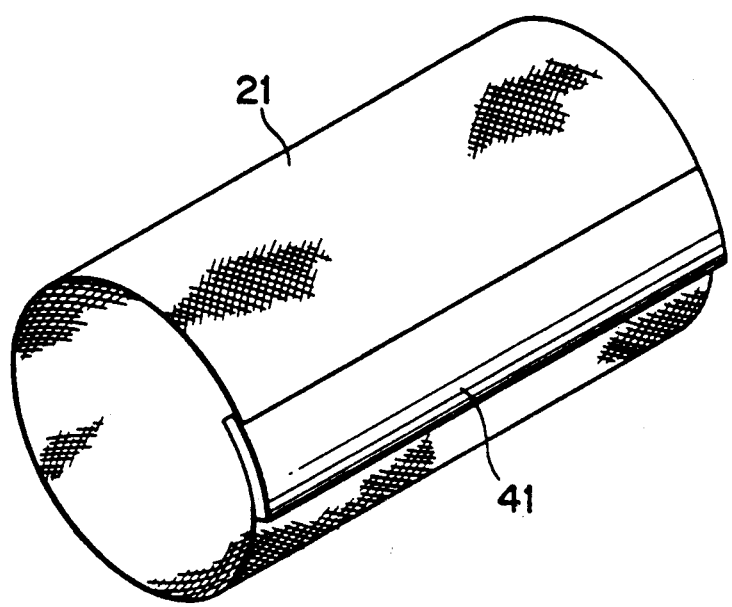
FIG. 2B is a perspective view of a modification of the shield member shown in FIG. 2A.

As shown in FIG. 2B, insulating members 41 may be interposed between two end portions of main shield member 21 which is formed by a single conductive member. In this case, generation of the eddy current in the main shield member can also be prevented.

Figure 3A:
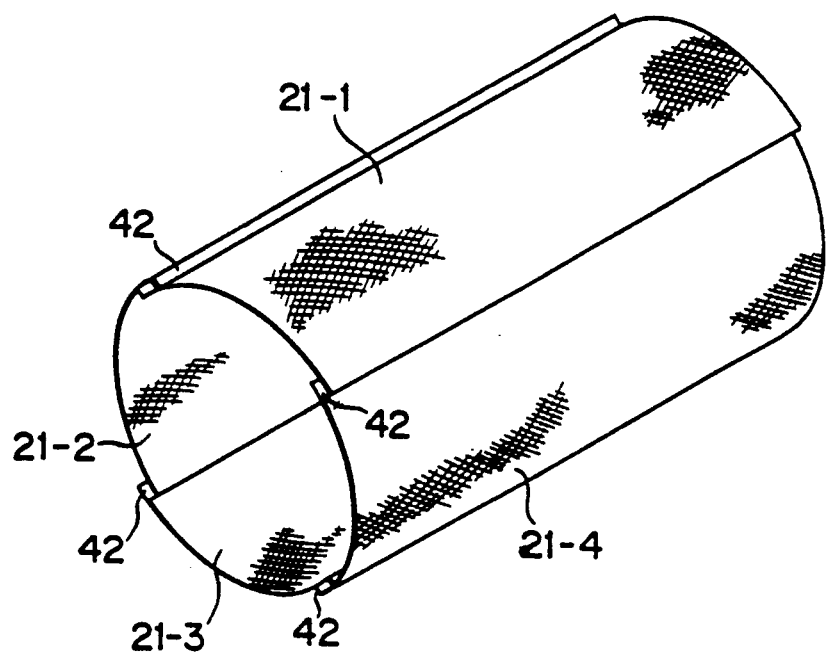
FIG. 3A is a perspective view of a shield member according to a second modification of the present invention.

FIG. 3A shows a second modification of the present invention.

In this modification, capacitors 42 are interposed between adjacent shield segments 21-1 to 21-4. Shield segments 21-1 to 21-4 and capacitors 42 constitute a RC circuit. The resonance frequency of the RC circuit is set at a value other than the frequency of the nuclear magnetic resonance signal. Thus, magnetic coupling between the RF coil and the main shield member can be avoided.

More specifically, as shown in FIG. 1C, RF coils 4 are arranged radially inside main shield member 21. When main shield member 21 is formed of a single conductive member, the frequency of a current flowing through the main shield member may be tuned to a frequency of a nuclear magnetic resonance signal. As a result, magnetic coupling occurs between the RF or receiving coil and the main shield member. An electric wave is thus emerged from the main shield member to the RF coil. For this reason, the nuclear magnetic resonance signal cannot be accurately received, and an MRI image is degraded.

Figure 3B:
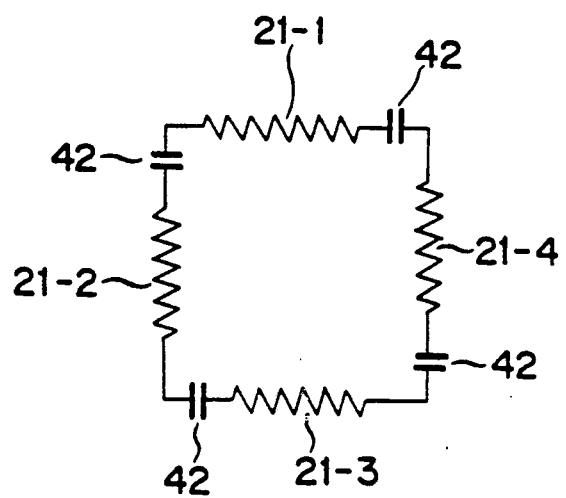
FIG. 3B is a circuit diagram of the shield member shown in FIG. 3A.

According to this modification, shield segments 21-1 to 21-4 and capacitors 42 constitute the RC circuit shown in FIG. 3B, and the resonance frequency of the RC circuit is set at a value other than the frequency of the magnetic resonance signal. The frequency of the current flowing through the main shield member is detuned to the frequency of the nuclear magnetic resonance signal. For this reason, no magnetic coupling is induced. The RF or receiving coil can accurately receive the nuclear magnetic resonance signal. In the second modification, generation of an eddy current can be prevented. When a switching speed of gradient magnetic field coils 3 correspond to a low frequency, the capacitors must have a large capacitance.

FIGS. 4A, 4B, and 4C show a third modification of the present invention.

In this modification, cover shield member 24 comprises planar member 43 which is formed of a flexible light-transmission material, e.g., an acrylic material, and is elastically deformable. Light-transmission conductive member 45, e.g., a metal net or expand metal is attached to the outer surface of member 43. As shown in FIG. 4A, cover shield member 24 is open before patient 10 is subjected to examination. As shown in FIG. 4B, when patient 10 is under examination, cover shield member 24 is bent and closed. Thus, the legs (a portion of a patient extending from the main shield member) of patient 10 are covered by cover shield member 24, and are electromagnetically shielded. In this modification, member 43 is formed of an acrylic member, and conductive member 45 is formed of, e.g., a metal net. Thus, a patient does not suffer from the feeling of oppression.

FIGS. 5A and 5B show a fourth modification of the present invention.

In this modification, cover shield member 24 is formed of a light-transmission conductive material such as a metal net or expand metal. The cover shield member is formed into a semi-cylindrical shape. When the intensity of a disturbance electromagnetic wave is relatively low, the cover shield member does not cover the entire legs (a portion of a patient extending from the main shield member) but covers the upper faces of the legs. In this modification, conductive member 44 is buried in base 7 of couch 6. Member 44 electromagnetically shields the lower face of patient 10. When the intensity of a disturbance electromagnetic wave is relatively high, both cover shield member 24 and conductive member 44 need only be used.

What is claimed is:

1. A magnetic resonance imaging system which has a Z axis passing through an object to be examined, comprising:
   first magnetic coil means, arranged radially outside said object, for applying a static magnetic field to said object along said Z axis, and for applying gradient magnetic fields to said objects;
   a cylindrical main shield member arranged radially inside said first magnetic coil means and extending along the said Z axis, to surround said object, said main shield member being connected to ground and being made of a conductive material;
   said first magnetic coil means and said main shield member having openings for enabling said object to be introduced into said main shield member, along said Z axis;
   second magnetic coil means, introduced between said main shield member and said object, through said openings of said first coil means and said main shield member, for transmitting a high frequency magnetic field signal to said object and receiving a magnetic resonance signal generated by said object;
   wherein said main shield member includes a plurality of shield segments formed of a conductive material, at least one of said plurality of shield segments being a perforated shield segment, and insulating members interposed between adjacent said shield segments, thereby preventing generation of an eddy current in said main shield member; and
   a cover shield member which is made of a conductive material, is electrically connected to said main shield member, and covers at least a portion of said object extending from said opening of said main shield member.

2. A magnetic resonance imaging system which has a Z axis passing through an object to be examined, comprising:
   first magnetic coil means, arranged radially outside said object, for applying a static magnetic field to said object along said Z axis, and for applying gradient magnetic fields to said object;
   a cylindrical main shield member arranged radially inside said first magnetic coil means and extending along said Z axis, to surround said object, said main shield member being connected to ground and being made of a conductive material;
   said first magnetic coil means and said main shield member having openings for enabling said object to be introduced into said main shield member, along said Z axis;
   second magnetic coil means, introduced between said main shield member and said object, through said openings of said first coil means and said main shield member, for transmitting a high frequency magnetic field signal to said object and receiving a magnetic resonance signal generated by said object;
   wherein said main shield member includes a single member formed of a conductive material and having two end portions, and an insulating member for connecting said two end portions of said single member, thereby preventing generation of an eddy current in said main shield member; and to cover shield member which is made of a conductive material, is electrically connected to said main shield member, and covers at least a portion of said object extending from said opening of said main shield member.

3. A magnetic resonance imaging system which has a Z axis passing through an object to be examined, comprising:

first magnetic coil means, arranged radially outside said object, for applying a static magnetic field to said object along said Z axis, and for applying gradient magnetic fields to said object;

a cylindrical main shield member arranged radially inside said first magnetic coil means and extending along said Z axis, to surround said object, said main shield member being connected to ground and being made of a conductive material;

said first magnetic coil means and said main shield member having openings for enabling said object to be introduced into said main shield member, along said Z axis;

second magnetic coil means, introduced between said main shield member and said object, through said openings of said first coil means and said main shield member, for transmitting a high frequency magnetic field signal to said object and receiving a magnetic resonance signal generated by said object;

wherein said main shield member includes a plurality of shield segments formed of a conductive material, and capacitors interposed between adjacent said shield segments, thereby preventing generation of magnetic coupling between said main shield member and said second magnetic coil means; and a cover shield member which is made of a conductive material, is electrically connected to said main shield member, and covers at least a portion of said object extending from said opening of said main shield member.

4. A system according to claim 1, 2 or 3, wherein said cover shield member is formed of a light-transmission material.

5. A system according to claim 1, 2 or 3, wherein said cover shield member is formed of a conductive fabric.

6. A system according to claim 1, 2 or 3, wherein said cover shield member includes an elastically deformable planar member, and a conductive member attached to one surface of said planar member.

7. A system according to claim 6, wherein said planar member and said conductive member are formed of a light-transmissive material.

8. A system according to claim 1, 2 or 3, wherein said cover shield member includes a conductive member which covers an upper surface of said object when said object is placed substantially horizontally.

9. A system according to claim 8, wherein said conductive member is formed of a light-transmissive material.

10. A system according to claim 8, wherein said system includes a patient couch, and said cover shield member includes a conductive member buried in said patient couch, whereby a lower surface of said object placed on said patient couch is electromagnetically shielded.

11. A magnetic resonance imaging system which has a Z axis passing through an object to be examined, comprising:

first magnetic coil means, arranged radially outside said object, for applying a static magnetic field to said object along said Z axis, and for applying gradient magnetic fields to said object;

a cylindrical main shield member arranged radially inside said first magnetic coil means and extending along said Z axis, to surround said object, said main shield member being connected to ground and being made of a conductive material;

said first magnetic coil means and said main shield member having openings for enabling said object to be introduced into said main shield member, along said Z axis;

second magnetic coil means, introduced between said main shield member and said object, through said openings of said first coil means and said main shield member, for transmitting a high frequency magnetic field signal to said object and receiving a magnetic resonance signal generated by said object;

wherein said main shield member includes a plurality of shield segments formed of a conductive material, at least one of said plurality of shield segments being a perforated shield segment, and insulating members interposed between adjacent said shield segments, thereby preventing generation of an eddy current in said main shield member; and a lid subshield member which closes one of said openings of said main shield member, said subshield member being electrically connected to said main shield member, and being made of a light-transmissive conductive material so as to allow light into said main shield member, thus minimizing feelings of oppression by a patient who is said object being examined.

12. A magnetic resonance imaging system which has a Z axis passing through an object to be examined, comprising:

first magnetic coil means, arranged radially outside said object, for applying a static magnetic field to said object along said Z axis, and for applying gradient magnetic fields to said object;

a cylindrical main shield member arranged radially inside said first magnetic coil means and extending along said Z axis, to surround said object, said main shield member being connected to ground and being made of a conductive material;

said first magnetic coil means and said main shield member having openings for enabling said object to be introduced into said main shield member, along said Z axis;

second magnetic coil means, introduced between said main shield member and said object, through said openings of said first coil means and said main shield member, for transmitting a high frequency magnetic field signal to said object and receiving a magnetic resonance signal generated by said object;

wherein said main shield member includes a plurality of shield segments formed of a conductive material, and capacitors interposed between adjacent said shield segments, thereby preventing generation of magnetic coupling between said main shield member and said second magnetic coil means; and a lid subshield member which closes one of said openings of said main shield member, said subshield member being electrically connected to said main shield member, and being made of a light-transmissive conductive material so as to allow light into said main shield member, thus minimizing feelings of oppression by a patient who is said object being examined.

13. A magnetic resonance imaging system which has a Z axis passing through an object to be examined, comprising:

first magnetic coil means, arranged radially outside said object, for applying a static magnetic field to said object along said Z axis, and for applying gradient magnetic fields to said object;

a cylindrical main shield member arranged radially inside said first magnetic coil means and extending along said Z axis, to surround said object, said main shield member being connected to ground and being made of a conductive material;

said first magnetic coil means and said main shield member having openings for enabling said object to be introduced into said main shield member, along said Z axis;

second magnetic coil means, introduced between said main shield member and said object, through said openings of said first coil means and said main shield member, for transmitting a high frequency magnetic field signal to said object and receiving a magnetic resonance signal generated by said object;

wherein said main shield member includes a plurality of shield segments formed of a conductive material, at least one of said plurality of shield segments being a perforated shield segment, and insulating members interposed between adjacent said shield segments; thereby preventing generation of an eddy current in said main shield member;

a cover shield member which is made of a conductive material, is electrically connected to said main shield member, and covers at least a portion of said object extending from said opening of said main shield member; and a lid subshield member which closes one of said openings of said main shield member, said subshield member being electrically connected to said main shield member, and being made of a light-transmissive conductive material so as to allow light into said main shield member, thus minimizing feelings of oppression by a patient who is said object being examined.

14. A magnetic resonance imaging system which has a Z axis passing through an object to be examined, comprising:

first magnetic coil means, arranged radially outside the object, for applying a static magnetic field to the object along the Z axis, and for applying gradient magnetic fields to the object;

a cylindrical main shield member arranged radially inside said first magnetic coil means and extending along the Z axis, to surround the object, said main shield member being connected to ground and being made of a conductive material, said first magnetic coil means and said main shield member having openings for enabling the object to be introduced into said main shield member, along the Z axis;

second magnetic coil means, introduced between said main shield member and the object, through the openings of said first coil means and said main shield member, for transmitting a high frequency magnetic field signal to the object and receiving a magnetic resonance signal generated by the object;

wherein said main shield member includes a single member formed of a conductive material and having two end portions, and an insulating member for connecting the two end portions of said member, thereby preventing generation of an eddy current in said main shield member.

15. A system according to claim 14, further comprising a lid subshield member which closes one of the openings of said main shield member, said subshield member being electrically connected to said main shield member, and being made of a light-transmission conductive material so as to allow light into said main shield member, thus minimizing feelings of oppression by a patient who is the object being examined.

* * * * *